United States Patent [19]
Kamiya et al.

[11] Patent Number: 5,780,047
[45] Date of Patent: Jul. 14, 1998

[54] PATCH

[75] Inventors: Tetsuro Kamiya; Kouichi Niinaka; Keiko Morioka; Hidenori Yorozu; Michitaka Sawada; Masaki Iwasaki, all of Tochigi, Japan

[73] Assignee: Kao Corporation, Tokyo, Japan

[21] Appl. No.: 671,543

[22] Filed: Jun. 27, 1996

[30] Foreign Application Priority Data

Jun. 27, 1995 [JP] Japan ................................ 7-160593
Feb. 9, 1996 [JP] Japan ................................ 8-024014

[51] Int. Cl.⁶ ........................... A61F 13/00; A61K 9/70
[52] U.S. Cl. ........................... 424/443; 424/447; 424/448
[58] Field of Search ........................... 424/443, 444, 424/445, 446, 447, 448, 449

[56] References Cited

U.S. PATENT DOCUMENTS 4,900,554  2/1990  Yanagibashi et al. ................. 424/448

FOREIGN PATENT DOCUMENTS 0 303 445   2/1989  European Pat. Off. .
0 701 822   3/1996  European Pat. Off. .
2 120 295   8/1972  France .
WO 95/05416  2/1995  WIPO .

*Primary Examiner*—Shelley A. Dodson
*Assistant Examiner*—Michael A. Williamson
*Attorney, Agent, or Firm*—Oblon, Spivak, McClelland, Maier & Neustadt, P.C.

[57] ABSTRACT

A patch is disclosed, which comprises a water-soluble adhesive sheet (a), and a patch is disclosed, which comprises a water-soluble adhesive sheet (a) and a water-soluble protective material (b) laminated thereon.

This patch is convenient in handling and achieves high merit. Also, it can be applied to the skin so as to exhibit excellent warm-bathing effects on the application site.

13 Claims, No Drawings

PATCH

FIELD OF THE INVENTION

This invention relates to a patch useful during bathing. More particularly, it relates to a patch which is convenient in handling, achieves high merit, and can be applied to the skin so as to exhibit excellent warm-bathing effect and skin-care effect at the application site. Also, the patch can be applied to human skin using hands or an instrument and then rubbed to obtain excellent bathing effect and skin-care effect.

BACKGROUND OF THE INVENTION

A number of bathing products of various types have been marketed which contain carbon dioxide and inorganic salts which can be dissolved in bathwater to enhance the warm-bathing effect; to mimic a "hot spring bath"; to deliver medicinal components and oily components efficacious in eczeme sudamen, eczema, atopic dermatitis, etc.; to enhance the color or aroma of the bath to make it more enjoyable; etc.

Before taking a bath, a standard dose of such a product is dissolved in the bathwater. Thus it enhances the warm-bathing effect, exerts its efficacy on various skin diseases or gives an enjoyable color or aroma. In Japan, it has been recognized that these bathing products are effective in treating various symptoms including blood circulation insufficiency, lumbago, fatigue, painful stiff neck and shoulder, neuralgia, rheumatism, eczeme sudamen, eczema, etc.

It is considered that these products enhance the warm-bathing effect as well as improve the systemic circulatory dynamics and metabolism, components present in the composition are also dispersed and dissolved in the bathwater further improving these effects, thus relieving the symptoms of the above-mentioned diseases.

Although these bathing preparations are mostly in the form of granules or tablets, some sheet-type or card-type products have recently been proposed. For example, JP-A-62-72609 and JP-A-62-72610 (the term "JP-A" as used herein means an "unexamined published Japanese patent application") describe a water-soluble, patch comprising pullulan optionally together with polyvinyl alcohol and/or polyvinyl pyrrolidone or a bathing preparation comprising various components packed in a bag made of a water-soluble sheet. However, this water-soluble bag is nothing but a bathing preparation merely having an improved solubility in bathwater.

Other sheet-type or card-type bathing preparations have been proposed by JP-A-62-81432, JP-A-1-290622, JP-A-1-313418, JP -A-2-202812, JP-A-4-103521, JP-A-4-124125, JP -A-4-321619, JP-A-4-321620, JP-A-5-294822, etc.

However, none of these conventional sheet-type bathing preparations allow application of the product to a specific location of the skin. Instead, these preparations aim merely at improving the solubility in bathwater, etc. These conventional bathing preparations and sheet-type bathing preparations can relieve topical symptoms (painful stiff neck and shoulder, lumbago, skin diseases such as eczema and atopy, etc.) to a certain extent, overall; however they cannot localize the effect to any specific body part. Attempts have been made to dissolve such a bathing preparation in an elevated amount in bathwater to thereby enhance its therapeutic effects. However, increasing the amounts of such products can cause increasing problems with safety, cost, other bathtub materials, the environment, etc. Accordingly, it is necessary to fundamentally reexamine the idea of bathing preparations in order to enhance the effects thereof.

On the other hand, patches and plasters have been used in the treatment of painful stiff neck and shoulder and lumbago. When a patch or plaster is used in a bathing system, however, the nonwoven fabric or woven fabric employed in the current outmost layer gets drenched, resulting in part or whole of the plaster agent fall into the bathwater and thereby soiling the bathwater. Alternatively, part of the plaster remains undissolved on the skin. Thus, these products are not usable in bathing.

SUMMARY OF THE INVENTION

Therefore, one object of the present invention is to provide a novel bathing preparation which can exert excellent effects of relieving topical symptoms of a human body (painful stiff neck and shoulder, lumbago, etc.).

Under these circumstances, the present inventors have conducted extensive studies to develop a novel bathing preparation which is capable of improving topical circulatory dynamics and metabolism and, if necessary, exerting medicinal effects on painful stiff neck and shoulder, lumbago and skin diseases, while giving favorable warm-bathing effects. As a result, they have successfully found out that when a patch, which comprises a water-soluble adhesive sheet containing appropriate bathing preparation component (s) blended with a water-soluble polymer optionally together with a non-adhesive water-soluble protective material laminated thereon, is applied on a human skin, the patch is gradually dissolved during bathing to thereby achieve excellent bathing effects at the application site without giving any insoluble matter in the bathwater, due to the water-soluble characteristics.

The patch of the present invention can be applied on the skin using hands or instrument and then rubbed, in a bathwater or outside the bathtub to obtain excellent bathing effect at the application site and circumference thereof.

Further, when a water-soluble adhesive sheet (a) is optionally used together with a water-soluble protective material (b) laminated on the sheet, a patch wherein the adhesive sheet (a) does not stick on the fingers and hands can be obtained. The present invention has been completed based on this finding.

Accordingly, the present invention provides a patch which comprises a water-soluble adhesive sheet (a). It further provides a patch which comprises a water-soluble adhesive sheet (a) and a water-soluble protective material (b) laminated thereon.

DETAILED DESCRIPTION OF THE INVENTION

Suitable materials useful as the water-soluble adhesive sheet (a) of the present invention should be soluble in water and have an adhesive enabling the application thereof to the skin. In the present invention, the patch preferably has an adhesiveness at such a level as defined below. Namely, when the patch of the present invention is applied on the skin at the extensor side of a forearm of a subject and then the forearm is allowed to stand horizontally while keeping the application site downward, the patch adheres to the skin for at least 10 seconds. A patch having an adhesiveness such that it falls off within 10 seconds might peel off from the skin during bathing.

To achieve both a sufficient adhesiveness and a solubility in water, it is preferable that the adhesive sheet (a) contains a water-soluble polymer and water.

Examples of suitable water-soluble polymer include water-soluble polymer compounds having salt-forming groups, nonionic water-soluble polymer compounds, gelatin and emulsion polymers such as acrylic resin emulsions.

Suitable nonionic water-soluble polymers include polydimethyl acrylamide, polyvinyl pyrrolidone, polyethylene glycol monomethacrylate, poly-2-ethyl-2-oxazoline, polyvinyl alcohol, pullulan, etc.

Water-soluble polymer compounds having salt-forming groups are particularly preferable, since they strongly adhere even to wet skin. The salt-forming groups of these water-soluble polymer compounds are not particularly restricted, so long as they can form salts in the presence of acid or base. Namely, either anionic, cationic or amphorteric groups are useable. Examples of suitable salt-forming groups include carboxyl, sulfonic acid residue, sulfuric acid residue, phosphoric acid residue, nitric acid residue, amino group and ammonium groups. Such a compound may have two or more salt-forming groups. Although it is preferable from the viewpoint of appearance that such the compound is highly soluble in water, a compound that is slightly insoluble can also be used.

Particular examples of suitable water-soluble polymer compounds having salt-forming groups include mucopolysaccharides (for example, hyarulonic acid, sodium hyarulonate, chondronitin sulfate, sodium chondroitin sulfate, cation-modified pullulan), hemicelluloses (for example, alginic acid, sodium alfiniare, ammoinum alginate, sodium carboxymethyl cellulose, sodium carboxymethyl amylose, cation-modified cellulose), etc.

Synthetic salt-forming compounds are preferred. Examples of suitable synthetic salt-forming compounds include polymers of one or more anionic, cationic or amphoteric monomers, copolymers of these monomers with other monomers, which are commonly employed in the art and free from any salt-forming group, such as vinyl carboxylates (vinyl acetate, etc.), (meth)acrylates (methyl methacrylate, etc.), alkyl vinyl ethers (methyl vinyl ether, etc.), N-vinyl cyclic amides (N-vinyl pyrrolidone, etc.), styrene, or alkyl-substituted styrene, and mixtures of these polymers.

Examples of suitable anionic monomers include monomers of unsaturated carboxylic acids (acrylic acid, methacrylic acid, maleic acid, itaconic acid, etc.) and anhydrides and salts thereof; monomers of unsaturated sulfonic acids (styrenesulfonic acid, 2-acrylamido-2-methylpropanesulfonic acid, etc.) or salts thereof; and monomers of unsaturated phosphates (vinylsulfonic acid, acid phosphoxyethyl (meth)acrylate, etc.).

Examples of suitable cationic monomers include (meth)acrylates or (meth)acrylamides having a dialkylamino group (dimethylaminoethyl acrylate, dimethylaminoethyl methacrylate, dimethylaminopropyl acrylamide, dimethylaminopropyl methacrylamide, etc.); styrenes having a dialkylamino group (dimethylaminostyrene, dimethylaminomethylstyrene, etc.); vinylpyridines (4-vinylpyridine, 2-vinylpyridine, etc.); and compounds obtained by quaternizing these compounds with the use of a well-known quaternizing agent (alkyl halide, benzyl halide, alkylsulfonic acid, arylsulfonic acid, dialkyl sulfate, etc.).

Examples of suitable amphoteric monomers include N-(3-sulfopropyl)-N-acryloyloxyethyl-N,N-dimethylammonium betaine, N-(3-sulfopropyl)-N-methacryloylamidopropyl-N, N-dimethylammonium betaine, N-(3-carboxymethyl)-N-methacryloylamidoprdpyl-N,N-dimethylammonium betaine, N-(3-sulfopropyl)-N-methacryloyloxyethyl-N,N-dimethylammonium betaine, N-carboxymethyl-N-methacryloyloxyethyl-N,N-dimethylammonium betaine, etc.

When the salt-forming group of such a polymer compound is not ionized, it is preferable to ionize it by neutralizing with an existing acid such as an inorganic acid (hydrochloric acid, sulfuric acid, etc.); an organic acid (acetic acid, propionic acid, lactic acid, succinic acid, glycolic acid, etc.) or a base such as a tertiary amine (trimethylamine, triethylamine, etc.), ammonia, sodium hydroxide, etc.

Preferred water-soluble polymer compounds having salt-forming groups include polymers obtained by polymerizing one or more cationic monomers, copolymers of such a monomer with an amphoteric monomer or another monomer which is commonly employed in the art and free from any salt-forming group. Such copolymers produce little skin irritation and are convenient to formulate.

Preferable examples of cationic monomers include (meth)acrylates or (meth)acrylamides having a dialkylamino group (dimethylaminoethyl acrylate, dimethylaminoethyl methacrylate, dimethylaminopropyl acrylamide, dimethylaminopropyl methacrylamide, etc.); and compounds obtained by quaternizing these compounds with the use of a well-known quaternizing agent (alkyl halide, benzyl halide, alkylsulfoic acid, arylsulfonic acid, dialkyl sulfate, etc.). Preferred monomers include dimethylaminoethyl methacrylate and its quaternized derivatives; quaternized dimethylaminopropyl acrylamide, copolymers of one or more monomers selected therefrom with the above-mentioned monomer(s) and mixtures thereof.

From the viewpoint of molding properties, the molecular weight of the water-soluble polymer having salt-forming groups preferably ranges from 10,000 to 3,000,000, still preferably from 100,000 to 2,000,000 as determine by weight average molecular weight.

This water-soluble polymer having salt-forming groups may be contained in the adhesive sheet (a) in an amount of from 1 to 99% (by weight, based on the total weight of the composition; the same will apply hereinafter), still preferably from 5 to 99%. These amounts vary depending on the water soluble polymer used.

When gelatin is used as a material for the adhesive sheet (a), the molecular weight is more preferably regulated by hydrolysis from 20,000–100,000 to the usual level of about 300,000 (i.e., high-molecular weight gelatin). A preferred method comprises blending a high-molecular weight gelatin with a low-molecular weight one to control the solubility. A gelatin having a low molecular weight of 20,000 or less is poor in gelling ability. Such a gelatin is preferably used together with a high-molecular weight gelatin. The content of the gelatin in the adhesive sheet (a) is preferably from 1 to 70%, still preferably from 5 to 40%, from the viewpoint of solubility and molding properties.

Preferable polyvinyl alcohol include a partly saponified one so as to elevate the solubility in water. However, it causes no problem to use a polyvinyl alcohol modified with various compounds (itaconic acid, etc.). The content of the polyvinyl alcohol in the adhesive sheet (a) preferably ranges from 1 to 60%, still preferably from 5 to 30%, from the viewpoint of solubility and molding properties.

The adhesiveness of the adhesive sheet (a) can be controlled by adjusting its water content. When completely dried, however, the adhesive sheet loses its adhesiveness. On the contrary, an excessively large water content is not desirable, since it is sometimes impossible in such a case to maintain the molding properties or stability. The water content of the adhesive sheet (a) is preferably from 0.1 to 60%, more preferably from 1 to 30%. The water content may be determined by measuring the weight loss due to drying at 80° C. or by the Karl Fisher method. To obtain accurate data, it is preferable to use the Karl Fisher method.

The adhesive sheet (a) may further contain polyol(s). Polyols can be added to achieve a plasticizing effect and improve the flexibility and molding properties of the plaster. Examples of suitable polyols include ethylene glycol, diethylene glycol, triethylene glycol, polyethylene glycol, propylene glycol, dipropylene glycol, butylene glycol, glycerol, sorbitol, mannitol, saccharose, diglycerol, etc. Among these polyols, propylene glycol, butylene glycol, glycerol, sorbitol or mannitol are preferred. Either one of these polyols or a mixture thereof may be employed. The content of the polyol(s) in the adhesive sheet preferably ranges from 1 to 80%, still preferably from 1 to 50%.

In the patch of the present invention, a sheet (b) comprising the water-soluble protective material may be provided on one side surface and/or the peelable sheet (c) may be provided on one side or both side surface(s), or the sheet (b) may be provided on one side surface and the peelable sheet (c) is provided on another side surface, in view of protection of the adhesive sheet (a) and convenience in handling upon application to human skin.

Also, when the (protective) sheet(s) (b) and/or (c) is not provided on one or both side of adhesive surfaces of the adhesive sheet, the patch of the present invention can be directly packed with a bag or package manufactured by an aluminum foil-laminated film.

The thickness of the water-soluble adhesive sheet (a) of the present invention preferably ranges from 5 to 10,000 μm, more preferably from 10 to 5,000 μm and most preferably from 20 to 1,000 μm.

In a second embodiment, the patch (a) of the present invention can give further improved handling property by using the water-soluble sheet (a) together with the water-soluble protective material (b) laminated on the sheet (a), which is preferable.

Suitable water-soluble protective material (b) useful in the present invention preferably comprise a water-soluble film, a water-soluble nonwoven fabric, a water-soluble woven fabric or a water-soluble nonwoven fabric or a water-soluble woven fabric with a water-soluble film laminated thereon. This water-soluble protective material (b) is adhered to one face of the water-soluble adhesive sheet (a).

This water-soluble protective material may be made of, for example, a film of gelatin, polyvinyl alcohol, pullulan, etc., a nonwoven fabric or a woven fabric. Also, examples of the material include a mixture of polyvinyl alcohol with a modified copolymer of vinyl acetate with an olefin or a vinyl monomer (vinyl carboxylate, etc.), a mixture of polyvinyl alcohol with a water-soluble or water-dispersible block copolymer, or a polyvinyl alcohol derivative modified by copolymerizing with itaconic acid, maleic acid, etc. A polyvinyl alcohol modified with gelatin, a water-soluble protein or a polysaccharide such as dextrin or pullulan can also be used.

Further, polyvinyl alcohol can be modified by an appropriate method to improve the compatibility with gelatin, a water-soluble protein or a polysaccharide such as dextrin or pullulan. That is to say, the water-soluble protective material (b) is one which has no adhesiveness per se, is capable of protecting one face of the water-soluble adhesive sheet (a) and can be molded into a film. Additives for improving the solubility in bathwater or the stability of the soluble material (b) can be used. In addition, the soluble protective material (b) can be modified to improve its moldability.

A sheet prepared by processing fibrous polyvinyl alcohol into a nonwoven fabric or a spun fabric illustrate a preferable example of the water-soluble protective material (b), since one face of the water-soluble adhesive sheet (a) of the present invention can be protected thereby. To obtain the fibrous polyvinyl alcohol, the same conditions (modification method, additives, etc.) as those described above regarding the polyvinyl alcohol film can be used. The fibrous polyvinyl alcohol may be any such one, so long as it has no adhesiveness per se, is soluble in cold or warm water and is capable of protecting the adhesive sheet (a). Examples of suitable fibrous polyvinyl alcohol sheet processed into a nonwoven fabric or a woven fabric include water-soluble polyvinyl alcohol fibers disclosed in JP-A-7-42019, JP-A-5-321105, JP-A-3-279410, JP-A-3-199408, JP-A-2-112406, etc. A nonwoven fabric or a woven fabric which is excellent in solubility, dissolution rate and dispersibility in water at low temperatures and shows little shrinkage even under a high humidity is preferably used.

The water-soluble protective material (b) is preferably applied in a thin layer such that it is soluble in cold or warm water and protects the adhesive sheet (a). The thickness preferably ranges from 1 to 3,000 μm, more preferably from 10 to 1,000 μm. It is preferable from the viewpoint of the object of the present invention to emboss the surface of a film or a nonwoven fabric to improve the solubility, etc.

The term "water-soluble" employed in the description of the sheet (a) and the protective material (b) of the present invention means that, when 1.5 to 15 g of the composition of the present invention is poured into 150 l of bathwater at 40° C., it is completely dissolved within 10 seconds to 15 minutes. Thus, the patch of the present invention can be completely dissolved during bathing so as to achieve warm-bathing effects.

For example, there are a method that when the peelable sheet(s) (c) are provided on the adhesive sheet (a), one peelable sheet (c) of one side is peeled off to apply to human body and then the peelable sheet (c) of another side is peeled off upon taking a bath to obtain the bathing effect; a method that when the sheet (b) is provided on one side surface of the adhesive sheet (a) and the peelable sheet (c) is provided on another side surface, the peelable sheet (c) of one side is peeled off to apply to human body and then to the maintained, as it is, upon taking a bath.

The peelable sheet (c) is not particularly restricted, so long as the sheet is a film having a high peelability. Namely, examples of the material of the peelable sheet (c) include a film comprising a resin selected from the group consisting of polyethylene, polyethyleneterephthalate, polypropylene, polystyrene, polyvinylchloride, polyvinyl alcohol and Saran; polyethylene-coated wood free paper; polyolefin-coated glassine paper; paper, aluminum thin film or the above resins, surface-treated with silicone. Among these, a film comprising resin of polyethylene or Saran is preferred. The thickness of the peelable sheet (c) is preferably from 1 to 500 μm, more preferably from 5 to 200 μm, most preferably from 20 to 100 μm in viewpoint of handling and cost.

The patch of the present invention may contain additional components commonly employed in bathing preparations. Moreover, it may contain drugs, dyes, pigments, vitamins, perfumes, enzymes, animal fats and oils such as lanolin and derivatives thereof, vegetable fats and oils such as jojoba oil and derivatives thereof, silicone compounds, various inorganic salts and inorganic compounds, organic acids, etc., though materials for bathing preparations usable herein are not restricted thereto.

Suitable inorganic compounds and organic salts include sodium chloride, potassium chloride, ammonium chloride, potassium sulfide, sodium sulfide, calcium oxide, magnesium oxide, potassium nitrate, sodium nitrate, calcium nitrate, iron subsulfide, metasilicic acid, silicic anhydride, neutral clay, sodium thiosulfate, sodium polyphosphate, sodium metaphosphate, sodium phosphate, calcium hydrogenphosphate, potassium bromide, slaked lime, sodium hyposulfite, calcium thiosulfate, sodium hydroxide, mica powder, boric acid, borax, sodium hydrogencarbonate, sodium sesquicarbonate, sodium carbonate, magnesium carbonate, sodium sulfate, magnesium sulfate, etc.

Suitable organic acids, esters and salts include adipic acid, benzoic acid, malic acid, tartaric acid, malonic acid, citric acid, lactic acid, fumaric acid, succinic acid, etc.

Suitable drugs, Chinese orthodox medicines and herbs include atractylodes rhizome, *Valeriana fauriei BRIQ.*, schizonepeta herba, magnolia bark, cnidii rhizoma, dried bitter orange peel, angelicae radix, jasmin, ginger, ginseng, cinnamon bark, *Paeonia lactiflora PALL.*, Japanese pepperming, scutellaria root, *Gardenia jasminoides ELLIS* foram grandflora, hoelen, acorus root, *Artemisia princeps PAMPAN.*, *Schisandra repanda*, angelicae dahuricae radix, houttuyniae herba, camphor, saffron, phellodendron bark, fennel, citrus unshiu peel, *Matricaria chamomilla L.*, *Prunus persica* leaf, rosemary, melissa, horse chestnut, arnica, sage, etc. and extracts thereof.

Suitable essential oils and perfumed oils include Japanese peppermint oil, jasmin oil, camphor oil, Cupressaceae oil, dried bitter orange peel oil, citrus unshiu oil, orange oil, *Citrus junos* oil, acorus root oil, lavender oil, bay oil, clove oil, rose oil, eucalyptus oil, lemon oil, thyme oil, peppermint oil, sage oil, bergamot oil, acorus root oil, pine oil, menthol, d,l-menthol, l-menthol, cineole, eugenol, citral, citronellol, citronellal, borneol, linalool, geraniol, phenylethyl alcohol, benzyl acetate, camphor, thymol, spirantol, pinene, terpenoid compounds, etc.

Suitable fats and oils include natural fats and oils such as rice bran oil, rice bran extract, olive oil, soybean oil, jojoba oil, avocado oil, almond oil, sesame oil, coconut oil, sunflower oil, castor oil, cacao oil, mink oil, beef tallow, lard, fish fat, evening primrose oil, rose hip oil, etc., and hardened oils obtained by hydrogenating these fats and oils and glyceride derivatives thereof; waxes such as carnauba wax, beeswax, lanolin, etc.; hydrocarbons such as liquid paraffin, paraffin, vaseline, squalane, etc.; higher fatty acids such as lauric acid, myristic acid, palmitic acid, behenic acid, oleic acid, linoleic acid, linolenic acid, lanolic acid, isostearic acid, etc.; higher alcohols such as lauryl alcohol, cetyl alcohol, stearyl alcohol, oleyl alcohol, cholesterol, 2-exyldecanol, etc. and ester derivatives thereof.

Suitable silicones include liquid oil, powder and resin.

Suitable dyes are listed in Tables I and II of synthetic organic food additives defined by Ordinance of the Ministry of Health and Welfare such as Blue No. 1, Blue No. 2, Yellow No. 4, Yellow No. 5, Green No. 3, Green No. 4, Green No. 204, Yellow No. 202 (1), etc. Natural dyes authorized as food additives such as chlorophyll, riboflavin, crosin, anthraquinone, cochineal, canthaxanthin, safflower, etc. can be also used.

Suitable vitamins include vitamin A, vitamin B, vitamin C, vitamin D, vitamin E, etc.

Suitable fine powders include those generally called cosmetic powders including polymers such as acrylic resin, styrene resin, epoxy resin, silicon resin, nylon, polyethylene, polypropylene, polyvinyl chloride, polyethylene terephthalate (PET), polytetrafluoroethane, etc. and copolymers thereof; calcium silicate, natural aluminum silicate, synthetic aluminum silicate, zeolite, titanium oxide, talc, kaolin, mica, bentonite, etc.

Suitable surfactants include anionic, cationic, nonionic, natural and synthetic surfactants, etc.

Other additives which can also be present include sinter, sulfur, casein, sodium salicylate, roasted rice bran, mica powder, dextrin, neutral clay, skim milk powder, urea, amino acids, etc.

In addition to the components as described above, the bathing composition of the present invention may further contain antiseptics (e.g., benzoate, sorbic acid, etc.), sequestering agents (EDTA, NTA, etc.), proteases, anti-inflammatory agents, agents imparting a cool feel, agents imparting a warm feel , etc., if necessary.

Among these additives, it is preferable to use an agent imparting a cool feel and/or an agent imparting a warm feel.

Examples of the agents imparting a cool feel which are usable in the present invention include the following ones:

(1) l-Menthol, camphor and thymol.

(2) A menthol derivative represented by the following formula:

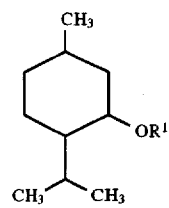

wherein $R^1$ represents an alkyl group having 1 to 8 carbon atoms, a monosaccharide residue,

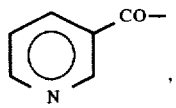

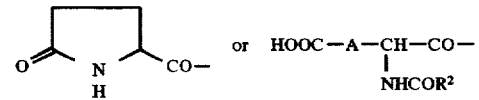

(wherein A represents a single bond or an alkylene group having 1 to 8 carbon atoms; and $R^2$ represents an alkyl group having 1 to 8 carbon atoms), or $HOOC\text{-}(CH_2)_m\text{-}CO\text{—}$ (wherein m is an integer of from 0 to 6).

(3) A compound represented by the following formula:

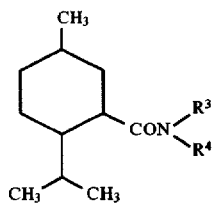

wherein $R^3$ and $R^4$ represent each a hydrogen atom, an alkyl group or a hydroxyalkyl group, having 1 to 8 carbon atoms.

(4) A monocyclic compound represented by the following formula:

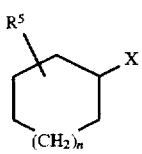

wherein X represents —OH, —COOH or

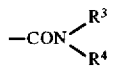

(wherein $R_3$ and $R_4$ are as defined above); $R^5$ represents a hydrogen atom or an alkyl group having 1 to 8 carbon atoms; and n is an integer of 0 to 5.

(5) A bridged bicyclic compound represented by the following formula:

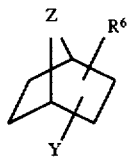

wherein Z is $(CH_2)_l$.

wherein Y represents —OH, —COOH or —COOR$^2$ (wherein $R^2$ is as defined above); $R^6$ represents a hydrogen atom or an alkyl having 1 to 8 carbon atoms; and l is 1 or 2.

(6) Tricyclic compounds represented by the following formulae:

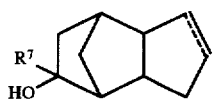

wherein $R^7$ represents a hydrocarbon group having 1 to 8 carbon atoms; and the dotted line represents a single or double bond; and

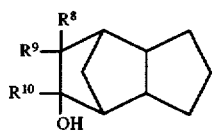

wherein either one of $R^8$ and $R^9$ represents a hydrogen atom while another represents a hydrocarbon group having 1 to 8 carbon atoms or both of $R^8$ and $R^9$ represent a hydrocarbon group having 1 to 8 carbon atoms, or $R^8$ and $R^9$ form together a ring having 2 to 6 carbon atoms; and $R^{10}$ represents a hydrogen atom or a hydrocarbon group having 1 to 8 carbon atoms.

(7) A tricyclic amide represented by the following formula:

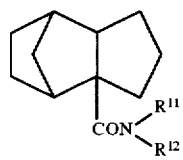

wherein $R^{11}$ and $R^{12}$ are the same or different and each represents a hydrogen atom, a hydrocarbon group which may be substituted by a hydroxy group, a lower alkoxy group or a lower alkoxycarbonyl group, or a phenyl group which may be substituted by a hydroxy group or a lower alkoxy group, or $R^{11}$ and $R^{12}$ may form a ring having 2 to 6 carbon atoms together with the adjacent nitrogen atom, which may contain further an oxygen atom.

The content of such an agent imparting a cool feeling in the sheet (a) preferably ranges from 0.01 to 20%, still preferably from 0.1 to 10%.

Examples of suitable agents imparting a warm feel include cayenne tincture, cayenne extract, cayenne powder, vanillylamide nonanoate, nicotinic acid derivatives (benzyl nicotinate, methyl nicotinate, phenyl nicotinate, tocopherol nicotinate, etc.), capsaicin, nasturtium officinale extract, *Zanthoxylum piperitum* extract, ginger extract, etc.

The content of such an agent imparting a warm feeling in the sheet (a) preferably ranges from 0.0001 to 20%, still preferably from 0.0005 to 5%.

The bathing composition of the present invention may be prepared in the following manner. The water-soluble adhesive sheet (a) is prepared by swelling a polymer in purified water, adding a plasticizer (glycerol, etc.) thereto and, if required, adding medicinal components, spreading the mixture on a flat plate and drying it at 60° to 120° C. Further, if necessary, a water-soluble protective material (b) (polyvinyl alcohol film, nonwoven fabric, etc.) is laminated thereon. After cooling, the obtained material is cut into pieces of an appropriate size. In an industrial production process, the adhesive sheet (a) is applied onto an appropriate, highly peelable film (c) and, after drying, if used, the water-soluble protective material (b) is laminated thereon.

As the highly peelable film as described above which is employed in order to protect the adhesive sheet (a), for example, a polyethylene terephthalate film, ethylene-coated woodfree paper, polyolefin-coated glassine paper or a polypropylene film, having been treated with silicone on one face for achieving a high releasability is used. The thickness of this film is usually 500 μm or less, preferably from 20 to 200 μm.

The bathing composition of the present invention is preferably packed in an airtight package material and stored to prevent deterioration in qualities due to moisture. Preferable examples of the airtight package material include cellophane, moistureproof cellophane, polypropylene, nylon, polyester, vinylidene chloride, vinyl chloride, polycarbonate, low-density polyethylene, high-density polyethylene, linear low-density polyethylene, ionomer, polyvinyl alcohol, ethylene/vinyl acetate copolymer, ethylene/acrylic acid copolymer, ethylene/ethyl acrylate copolymer, polymethylpentene, polystyrene, aluminum foil, etc. Among these materials, films having polypropylene, vinylidene chloride, low-density polyethylene, high-density polyethylene, linear low-density polyethylene or aluminum foil laminated thereon are particularly preferable due to their excellent barrier properties to vapor permeation. Regarding the barrier properties to vapor permeation, it is preferable that the packed product scarcely suffers from any change in weight when stored at 40° C./80% RH. The package material for the patch of the present invention preferably results in a weight change of the product of not more than ±5%, when stored under the above-mentioned conditions for 6 months.

The patch of the present invention can be used with a bathing method which not only the patch is immersed into the bathwater but also the patch is wetted by shower or sauna (steam bath).

The patch of the present invention may be poured into bathwater and dissolved therein followed by bathing. However, it is still preferable to apply the patch of the present invention to, for example, the shoulder or lower back followed by bathing.

Also, when the bathing method such as shower or sauna in which the patch is not immersed in the bathwater is used, the bathing composition can be applied on the skin of human body and then rubbed using hands or instrument. Examples of the instrument include sponge or body brush.

By laminating the water-soluble protective material on the water-soluble adhesive sheet, a patch which is soluble in bathwater and shows a high adhesiveness and good handling properties without sticking to fingers is provided.

Although the patch of the present invention may be poured as such into bathwater, its adhesiveness to the skin enables the application thereof to the specific areas of the body such as the shoulder or lower back. Thus topical circulatory dynamics and metabolism can be improved and medicinal effects can be exerted on painful stiff neck and shoulder, lumbago and skin diseases, while giving favorable warm-bathing effects.

In the patch of the present invention, the components are dispersed or dissolved in bathwater to thereby simultaneously achieve systemic effects (bathing effects, skin-care effects, etc.) and topical effects of relieving various symptoms.

Different from the existing patches and plasters, the patch of the present invention is solubilized in bathwater. It is therefore unnecessary to peel off the plaster from the skin after using, which brings a good feel in use.

As the patch can be used with the bathing method such as shower or sauna (steam bath) that the bathing composition is not immersed in the bathwater, the bathing composition has excellent convenience in handling, and when the bathing composition is applied on the human body and then rubbed, the effect due to the bathing composition can be provided to the whole body and further the same effect (i.e., topical effect of relieving various symptoms due to application to the body) as in the bathing method in which the bathing composition is immersed in bathwater can be obtained.

EXAMPLE

To further illustrate the present invention in greater detail, and not by way of limitation, the following Examples will be given.

Formulation Examples (Examples 1, 2 and 5)

In accordance with each formulation as given in Table 1 (a), purified water was added to gelatin. After allowing the gelatin to swell at room temperature, the mixture was heated to 60° C. and the remaining components listed in Table 1 (a) were added with stirring. After mixing, the mixture was spread into a sheet of 1.5 mm in thickness. Next, a polyvinyl alcohol film (degree of polymerization: 1,500) of 30 µm in thickness listed in Table 1 (b) or a water-soluble nonwoven fabric (fiber diameter: 15 µm, fiber dissolution temperature: 1° C. nonwoven fabric thickness: 280 µm, nonwoven fabric Metsuke: 50 g/m$^2$) comprising maleic acid-modified polyvinyl alcohol (degree of polymerization: 1,400) was laminated thereon. After solidifying, the obtained sheet was cut into pieces (7×12 cm; about 15 g) and packed in an aluminum laminate film bag.

Example 3

In accordance with the formulation as given in Table 1 (a), purified water was added to gelatin. After allowing the gelatin to swell at room temperature, the mixture was heated to 60° C. Then an aqueous solution of polyacrylic acid (purity: 10%) and sodium polyacryalte were added thereto and the mixture was thickened under stirring. Next, the remaining components listed in Table 1 (a) were added. After mixing, the mixture was spread into a sheet of 1.5 mm in thickness. Next, a polyvinyl alcohol film (degree of polymerization: 1,500) listed in Table 1 (b) of 30 µm in thickness or an Oblate (wafer) film of 30 µm in thickness was laminated thereon. After solidifying, the obtained sheet was cut into pieces (7×12 cm; about 15 g) and packed in an aluminum laminate film bag.

Example 4

Purified water was added to polyvinyl alcohol shown in Table 1 (a). After allowing the polyvinyl alcohol to swell, the mixture was heated to 70° C. and thickened under stirring. Then the remaining components listed in Table 1 (a) were added. After mixing, the mixture was spread into a sheet of 1.5 mm in thickness. Next, a polyvinyl alcohol film of 30 µm in thickness listed in Table 1 (b) was laminated thereon. After solidifying, the composite sheet was cut into pieces (7×12 cm; about 15 g) and packed in an aluminum laminate film bag.

TABLE 1

|  | Ex. 1 | Ex. 2 | Ex. 3 | Ex. 4 | (wt %) Ex. 5 |
|---|---|---|---|---|---|
| (a) | | | | | |
| Gelatin | 15.0 | 15.0 | 10.0 | | 15.0 |
| Polyvinyl acid | | | | 15.0 | |
| Polyacrylic acid | | | 1.0 | | |
| Sodium polyacrylate | | | 2.0 | | |
| Carboxyvinyl polymer | | | | 1.0 | |
| Acrylic resin emulsion | | 1.0 | 1.0 | | |
| Menthol | 0.3 | 0.3 | 0.3 | 0.3 | 0.1 |
| Camphor | 0.3 | 0.3 | 0.3 | 0.3 | 0.1 |
| Cayenne tincture | 1.0 | 1.0 | 1.0 | 1.0 | |
| Methyl salicylate | 0.5 | 0.5 | 0.5 | 0.5 | |
| Dipotassium glycyrrhetinate | | | | | 1.0 |
| German chamomile extract | | | | | 2.0 |
| Propylene glycol | 30.0 | 30.0 | 30.0 | | 40.0 |
| Glycerol | 10.0 | 10.0 | 10.0 | 5.0 | |
| Sorbitol | | | | | 5.0 |
| Perfume | 0.4 | 0.4 | 0.4 | 0.4 | 0.4 |
| Menthol | 0.3 | 0.3 | 0.3 | 0.3 | 0.1 |
| Sodium benzoate | 0.3 | 0.3 | 0.3 | 0.3 | 0.3 |
| Purified water | balance | ← | ← | ← | ← |
| (b) | | | | | |
| Polyvinyl alcohol film | 0.4 | | 0.4 | 0.4 | |
| Polyvinyl alcohol nonwoven fabric | | 0.4 | | | 0.4 |

Examples 6 to 10

A patch was prepared from each of the products of Examples 1 to 5 without covering with a protecting material listed in Table 1 (b). After solidifying, the obtained sheet was cut into pieces (7×12 cm) and packed in an aluminum laminate film bag.

Test Example 1

The patch of Examples 1 to 10 were examined by 10 panelists.

(Method)

Before bathing, the aluminum laminate film bag was broken and then the patch was taken out therefrom was applied to the shoulder. Then effects on painful stiff neck and shoulder and solubility into bathwater and the convenience in use were evaluated during and after bathing.

(Result)

Tables 2 to 4 show the results wherein each number represents the number of the panelists presenting the given evaluation.

TABLE 2

Effect on painful stiff neck and shoulder (during bathing)

|  | Very Efficacious | Efficacious | Somewhat Efficacious | Not Efficacious |
|---|---|---|---|---|
| Example 1 | 6 | 3 | 1 | 0 |
| Example 2 | 7 | 2 | 1 | 0 |
| Example 3 | 6 | 4 | 0 | 0 |
| Example 4 | 6 | 3 | 0 | 1 |
| Example 5 | 7 | 1 | 1 | 1 |
| Example 6 | 5 | 3 | 2 | 0 |
| Example 7 | 7 | 2 | 1 | 0 |
| Example 8 | 5 | 5 | 0 | 0 |
| Example 9 | 6 | 1 | 3 | 0 |
| Example 10 | 7 | 0 | 2 | 1 |

TABLE 3

Effect on painful stiff neck and shoulder (after bathing)

|  | Very Efficacious | Efficacious | Somewhat Efficacious | Not Efficacious |
|---|---|---|---|---|
| Example 1 | 8 | 2 | 0 | 0 |
| Example 2 | 6 | 3 | 1 | 0 |
| Example 3 | 5 | 3 | 2 | 0 |
| Example 4 | 7 | 1 | 1 | 1 |
| Example 5 | 6 | 0 | 3 | 1 |
| Example 6 | 7 | 3 | 0 | 0 |
| Example 7 | 4 | 3 | 2 | 1 |
| Example 8 | 5 | 3 | 1 | 1 |
| Example 9 | 4 | 3 | 2 | 1 |
| Example 10 | 7 | 0 | 1 | 2 |

TABLE 4

Solubility into bathwater

|  | Slight Fast | Suitable Solubility | Slight Slow | Not Dissolved |
|---|---|---|---|---|
| Example 1 | 1 | 7 | 2 | 0 |
| Example 2 | 1 | 8 | 1 | 0 |
| Example 3 | 2 | 7 | 1 | 0 |
| Example 4 | 0 | 9 | 1 | 0 |
| Example 5 | 1 | 8 | 1 | 0 |
| Example 6 | 1 | 7 | 2 | 0 |
| Example 7 | 0 | 6 | 4 | 0 |
| Example 8 | 1 | 8 | 1 | 0 |
| Example 9 | 3 | 7 | 0 | 0 |
| Example 10 | 2 | 6 | 2 | 0 |

As is apparent from the above results, the patch of the present invention is highly efficacious in relieving painful stiff neck and shoulder and dissolubility. In addition, it is extremely convenient to use, in case of Examples 6 to 10 that it is covered with a protective material made of a water-soluble film.

Examples 11 to 19

In accordance with the formulation of the following Table 5 (a), purified water was added to each polymer. After allowing each to swell at room temperature, the remaining components listed in Table 5 (a) were added thereto under stirring. After mixing, the mixture was spread onto a polyethylene film with silicone-treated surface to give a sheet of about 1.5 mm in thickness. Then it was introduced into a dryer at 110° C. During drying, the samples were taken with the passage of time followed by the determination of the water content by the Karl Fisher method. Thus the spread plaster was semidried until the water content reached 15%. Next, a sheet, which consisted of a water-soluble nonwoven fabric (fiber diameter: 15 µm, fiber dissolution temperature: 1° C., nonwoven fabric thickness: 170 µm, nonwoven fabric Metsuke: 25 g/m$^2$) comprising maleic acid-modified polyvinyl alcohol (degree of polymerization: 1,400) shown in Table 5 (b) and a polyvinyl alcohol film (degree of polymerization: 1,500) adhered thereto, was laminated on the semidried sheet. Then the obtained product was cut into pieces (10×7 cm) and packed in (c) a package material made of a polyethylene film provided with an aluminum foil laminated thereon.

TABLE 5

(a) Formulation of water-soluble adhesive sheet

| Component | Examples 6 to 12 | Example 13 | (wt %) Example 14 |
|---|---|---|---|
| Polymer (Examples 6 to 14) | 40 | 40 | 40 |
| Propylene glycol | — | 5 | 10 |
| L-menthol | 1 | 1 | 1 |
| Camphor | 1 | 1 | 1 |
| Cayenne tincture | 1 | 1 | 1 |
| Glycol salicylate | 1 | 1 | 1 |
| Methylparaben | 0.15 | 0.15 | 0.15 |
| Butylparaben | 0.15 | 0.15 | 0.15 |
| Purified water | balance | ← | ← |

Examples 11, 18

Poly-2-acrylamido-2-methylpropanesulfonic acid (m.w.: 500,000).

Examples 12, 19

Polymethacryloyloxymethylsuccinic acid (m.w.: 200,000).

Example 13

Sodium styrenesulfonate polymer (m.w.: 100,000).

Example 14

Methacrylic acid polymer (m.w.: 200,000).

Example 15

Polymethacryloyloxyethyltrimethylammonium chloride (m.w.: 400,000).

Example 16

Polymethacryloyloxyethyldimethylammonium diethylsulfate (m.w.: 300,000).

Example 17

Polymethacryloylamidopropyltrimethylammonium chloride (m.w.: 300,000)/polyacrylamidopropyltrimethylammonium chloride (m.w.: 300,000) copolymer.

(b) Water-soluble protective material

A sheet consisting of a water-soluble nonwoven fabric (fiber diameter: 15 μm, fiber dissolution temperature: 1° C., nonwoven fabric thickness: 170 μm, nonwoven fabric Metsuke: 25 g/m²) comprising maleic acid-modified polyvinyl alcohol (degree of polymerization: 1,400) and a polyvinyl alcohol film (degree of polymerization: 1,500) adhered thereto.

(c) Airtight package material

A polyethylene film provided with an aluminum foil laminated thereon.

Test Example 2

The patches of the present invention prepared in the above Examples 11 to 19 were subjected to a bathing test wherein each sample was applied to the shoulder or lower back (dry skin and wet skin after cleansing with a soap) of 5 subjects. Thus the adhesiveness to the skin and the solubility in the bathwater of each preparation was evaluated.

As a result, none of the patches of the present invention of Examples 11 to 19 peeled off from the dry or wet skin in bathing, which indicates that these preparations are excellent in adhesiveness. And each of them was excellent in the solubility in the bathwater and no insoluble matter was observed, which indicates that these preparations are highly useful in practice.

Example 20

In accordance with the formulation described in Example 19, purified water was added to the polymer. After swelling at room temperature, the remaining components were added under stirring. After mixing, the mixture was spread onto a polyethylene film with silicone-treated surface to give a sheet of about 1.5 mm in thickness. Then it was introduced into a dryer at 110° C. During drying, samples were taken and the water content of each was determined by the Karl Fisher method. Thus the spread plaster was semidried until the water content reached 15%. Next, a polyethylene film with silicone-treated surface was laminated on the semidried sheet. Then the obtained product was cut into pieces (10×7 cm) and packed in a package material made of a polyethylene film provided with an aluminum foil laminated thereon. The layer system of this Example consists of a water-soluble adhesive sheet (a) provided with water-insoluble, highly peelable sheets (c) laminated on both faces thereof. After peeling off one of the peelable sheet, the preparation is applied to the shoulder and then another peelable sheet is peeled off to thereby prevent fingers from stickiness of the adhesive sheet.

While the invention has been described in detail and with reference to specific embodiments thereof, it will be apparent to one skilled in the art that various changes and modifications can be made therein without departing from the spirit and scope thereof.

The present application is based on JP 07-160593 filed on Jun. 27, 1995, the full text of which is incorporated herein by reference.

What is claimed is:

1. A patch comprising a water-soluble adhesive sheet (a) and a water-soluble protective material (b) laminated thereon selected from the group consisting of a non-ionic water-soluble polymer, a gelatin and an emulsion polymer,
   wherein said non-ionic water-soluble polymer is polydimethyl acrylamide, polyvinyl pyrrolidone, polyetylene glycol monomethacrylate, poly-2-ethyl-2-oxazoline, polyvinyl alcohol or pullulan,
   said gelatin has a weight average molecular weight of 20,000 to 100,000, and
   wherein said emulsion polymer is an acralate resin emulsion.

2. A patch of claim 1 comprising a water-soluble adhesive sheet (a) wherein a sheet (b) comprising the water-soluble protective material is provided on one side surface of said adhesive sheet (a) and a peelable sheet (c) is provided on another side surface of said adhesive sheet (a).

3. A patch of claim 1 comprising a water-soluble adhesive sheet (a) wherein a peelable sheets (c) are provided on both side surface of said adhesive sheet (a).

4. The patch of claim 1, wherein said water-soluble adhesive sheet (a) comprises a water-soluble polymer and water.

5. The patch of claim 1, wherein said water-soluble adhesive sheet (a) further comprises a polyol.

6. The patch of claim 1, wherein said water-soluble adhesive sheet (a) further comprises an agent imparting a cool feel and/or an agent imparting a warm feel.

7. The patch of claim 1, wherein said water-soluble adhesive sheet (a) has a thickness from 5 to 10,000 μm.

8. The patch of claim 1, wherein said water-soluble protective material (b) comprises a water-soluble film, a water-soluble nonwoven fabric, a water-soluble woven fabric or a water-soluble nonwoven fabric or a water-soluble woven fabric with a water-soluble film laminated thereon.

9. The patch of claim 4, wherein said water-soluble protective material (b) comprises a water-soluble film, a water-soluble nonwoven fabric, a water-soluble woven fabric or a water-soluble nonwoven fabric or a water-soluble woven fabric with a water-soluble film laminated thereon.

10. The patch of claim 1, wherein said water-soluble protective material (b) has a thickness from 1 to 3,000 μm.

11. The patch of claim 1, further comprising an additive selected from the group consisting of a drug, dye, pigment, vitamin, perfume, enzyme, animal fat, animal oil, silicone compounds, and inorganic compounds.

12. A method of bathing which comprises applying a patch on skin comprising:
   a water-soluble adhesive sheet (a) and a water-soluble protective material (b) laminated thereon selected from the group consisting of a non-ionic water-soluble polymer, a gelatin and an emulsion polymer,
   wherein said non-ionic water-soluble polymer is polydimethyl acrylamide, polyvinyl pyrrolidone, polyethylene glycol monomethacrylate, poly-2-ethyl-2-oxazoline, polyvinyl alcohol or pullulan,
   said gelatin has a weight average molecular weight of 20,000 to 100,000, and
   wherein said emulsion polymer is an acrylate resin emulsion.

13. A method which of bathing which comprises pouring a patch into bathwater comprising:
   a water-soluble adhesive sheet (a) and a water-soluble protective material (b) laminated thereon selected from the group consisting of a non-ionic water-soluble polymer, a gelatin and an emulsion polymer,
   wherein said non-ionic water-soluble polymer is polydimethyl acrylamide, polyvinyl pyrrolidone, polyethylene glycol monomethacrylate, poly-2-ethyl-2-oxazoline, polyvinyl alcohol or pullulan, said gelatin has a weight average molecular weight of 20,000 to 100,000, and wherein said emulsion polymer is an acrylate resin emulsion.

* * * * *